(12) United States Patent
Tominaga et al.

(10) Patent No.: US 9,399,051 B2
(45) Date of Patent: Jul. 26, 2016

(54) DIPEPTIDYL PEPTIDASE-4 INHIBITOR

(71) Applicant: Kaneka Corporation, Osaka (JP)

(72) Inventors: Yuji Tominaga, Takasago (JP); Shinichi Yokota, Takasago (JP); Hozumi Tanaka, Takasago (JP); Hideyuki Kishida, Takasago (JP); Masayasu Kitagawa, Takasago (JP); Hiroshi Tachi, Tokyo (JP); Toru Ota, Iwate (JP)

(73) Assignee: Kaneka Corporation, Osaka (JP)

( * ) Notice: Subject to any disclaimer, the term of this patent is extended or adjusted under 35 U.S.C. 154(b) by 150 days.

(21) Appl. No.: 14/171,121

(22) Filed: Feb. 3, 2014

(65) Prior Publication Data

US 2014/0142036 A1    May 22, 2014

Related U.S. Application Data

(62) Division of application No. 13/388,913, filed as application No. PCT/JP2010/004872 on Aug. 3, 2010, now abandoned.

(30) Foreign Application Priority Data

Aug. 3, 2009    (JP) .................. 2009-180829

(51) Int. Cl.

| A61K 35/66 | (2015.01) |
|---|---|
| A61P 3/10 | (2006.01) |
| C12P 21/06 | (2006.01) |
| A61K 38/16 | (2006.01) |
| A23L 1/30 | (2006.01) |
| A23L 1/305 | (2006.01) |
| A61K 36/48 | (2006.01) |

(52) U.S. Cl.
CPC ............. *A61K 38/168* (2013.01); *A23L 1/30* (2013.01); *A23L 1/3053* (2013.01); *A61K 36/48* (2013.01); *C12P 21/06* (2013.01); *C12Y 304/14005* (2013.01); *Y02P 20/52* (2015.11)

(58) Field of Classification Search
None
See application file for complete search history.

(56) References Cited

U.S. PATENT DOCUMENTS

| 6,299,911 B1 | 10/2001 | Kawabata et al. |
|---|---|---|
| 2006/0052382 A1 | 3/2006 | Duffy et al. |
| 2009/0155239 A1 | 6/2009 | Nakamura |

FOREIGN PATENT DOCUMENTS

| CN | 1261917 A | 8/2000 |
|---|---|---|
| CN | 1275083 A | 11/2000 |
| JP | 57-186450 A | 11/1982 |
| JP | 11-075765 A | 3/1999 |
| JP | 2000-072687 A | 3/2000 |
| JP | 2000-327689 A | 11/2000 |
| JP | 2001-186877 A | 7/2001 |
| JP | 2002-027979 A | 1/2002 |
| JP | 2002-237978 A | 8/2002 |
| JP | 2004-166628 A | 6/2004 |
| JP | 2004-535455 A | 11/2004 |
| JP | 2004-536115 A | 12/2004 |
| JP | 2005-500321 A | 1/2005 |
| JP | 2005-325062 A | 11/2005 |
| JP | 2006-296251 A | 11/2006 |
| JP | 2007-039424 A | 2/2007 |
| JP | 2007-277163 A | 10/2007 |
| JP | 2008-500304 A | 1/2008 |
| JP | 2008-239521 A | 10/2008 |
| JP | 2008-239522 A | 10/2008 |
| JP | 2008-280291 A | 11/2008 |
| WO | WO-9902705 A1 | 1/1999 |
| WO | WO-03/002553 A2 | 1/2003 |
| WO | WO-03/004012 A1 | 1/2003 |
| WO | WO-03/004498 A1 | 1/2003 |
| WO | WO-2004/058266 A1 | 7/2004 |
| WO | WO-2005117933 A1 | 12/2005 |
| WO | WO-2008/066070 A1 | 6/2008 |

OTHER PUBLICATIONS

Hiroyuki Fujita JP 2002-027978 translation for USPTO by Phoenix translations, Mar. 2016.*
Journal of Pharmacological Sciences, 2005, vol. 125, p. 379-384 with translation of Abstract.
Expert Opinion Investig. Drugs, "Inhibitors of dipeptidyl peptidase IV: a novel approach for the prevention and treatment of Type 2 diabetes?", 2004, 13(9), p. 1091-1102.
Sun et al., "The Present Situation of Douchi, Natto and Tempeh", China Condiment, No. 3, p. 29-33 (2008).
Reynolds, "Fixed-dose combination of sitagliptin and metformin for the treatment of type 2 diabetes", Diabetes, Metabolic Syndrome and Obesity: Targets and Therapy 2: 127-134, 2009.
Tachi et al., "An x-prolyl dipeptidyl-aminopeptidase from aspergillus oryzae", Phytochemistry, vol. 31, No. 11, pp. 3707-3709, 1992.

* cited by examiner

*Primary Examiner* — Emily Cordas
(74) *Attorney, Agent, or Firm* — Polsinelli PC

(57) ABSTRACT

The present invention aims to provide a DPP-4 inhibitor that is obtained by using a food as a raw material and that is suitable for oral ingestion from the viewpoints of flavor and absorbability, and a composition for the prevention and/or amelioration of diabetes which contains the DPP-4 inhibitor. The present invention provides a DPP-4 inhibitor obtained by treating an azuki bean or a kidney bean with a microorganism or a proteolytic enzyme produced by the microorganism. In particular, a preferable DPP-4 inhibitor can be obtained by hydrolyzing an azuki bean with a koji mold or a proteolytic enzyme derived from the koji mold to fragment a protein in the azuki bean.

2 Claims, No Drawings

DIPEPTIDYL PEPTIDASE-4 INHIBITOR

CROSS-REFERENCE TO RELATED APPLICATIONS

This application is a continuation application of U.S. application Ser. No. 13/388,913, filed on Feb. 3, 2012, which is a 35 U.S.C. 371 Application of International Application No. PCT/JP2010/004872, filed Aug. 3, 2010, claiming priority from Japanese Patent Application No. 2009-180829, filed Aug. 3, 2009, the entire contents of which are herein incorporated by reference.

The present invention relates to a dipeptidyl peptidase-4 inhibitor, and a production method thereof. The present invention also relates to an agent for preventing and/or ameliorating diabetes which contains the dipeptidyl peptidase-4 inhibitor.

TECHNICAL FIELD

Background Art

Dipeptidyl peptidase-4 (hereinafter referred to as DPP-4) is a type of serine protease that recognizes the second proline or alanine from the N-terminal of a peptide and severs it from the peptide. DPP-4 is widely distributed in mammalian tissues, and is known to be present in the kidneys, liver, intestinal epithelium, placenta and plasma in particular. Although the role of DPP-4 in mammals is not completely clear, it is thought to play an important role in processes such as the metabolism of neuropeptides, activation of T cells, adhesion of cancer cells to endothelial cells, and cellular invasion of HIV. Substrates of DPP-4 are known to include peptides associated with nutrition, metabolism, the immune system and sensation of pain. In particular, DPP-4 is attracting attention as an enzyme that deactivates glucagon-like peptide-1 (hereinafter referred to as GLP-1), which functions to enhance glucose-dependent insulin secretion, and gastric inhibitory polypeptide or glucose-dependent insulinotropic peptide (Non-Patent Document 1).

In addition to the glucose-dependent secretion of insulin from pancreatic β cells, examples of other physiological effects of GLP-1 include glucagon secretion inhibitory effect, pancreatic β cell protective and proliferative effects, inhibition of gastric emptying, and activation of glycogen synthase in the liver. Moreover, GLP-1 also causes a reduction in food intake by acting on the satiety center of the hypothalamus in the central nervous system (Non-Patent Document 2).

The physiological activity of GLP-1, such as the glucose concentration-dependent promotion of insulin secretion, is also known to be enhanced by inhibiting degradation of GLP-1, for example, through inhibition of DPP-4 activity. On the basis of these facts, a compound having DPP-4 inhibitory effect is expected to demonstrate any effect on glucose intolerance, postprandial hyperglycemia, fasting hyperglycemia and accompanying obesity and diabetes complications, and other symptoms observed in type 1 diabetes, type 2 diabetes and the like. In addition, it is also expected to demonstrate an effect that assists the supply of energy to muscles during exercise because of its ability to promote insulin secretion to promote the uptake of sugar into muscles.

DPP-4 is also involved in the metabolism of neuropeptides such as neuropeptide Y, endomorphin-1, endomorphin-2 and substance P. Thus, a compound that inhibits DPP-4 can be expected to serve as a therapeutic for schizophrenia, depression, anxiety, epilepsy or a stress-related disease, or an analgesic by inhibiting the degradation of these physiologically active peptides. Moreover, since DPP-4 is also known to be involved in processes such as the metabolism of various cytokines and chemokines, activation of immunocompetent T cells, adhesion of cancer cells to endothelium, and proliferation of blood cells, a compound that inhibits DPP-4 is thought to be useful for preventing and/or ameliorating, through these effects, not only diabetes but also diseases such as rheumatoid arthritis, autoimmune diseases, allergic diseases such as asthma and food allergies, cancers, cancer metastasis, HIV infection, anemia and thrombocytopenia.

Many compounds obtained by chemical synthesis have been reported to be DPP-4 inhibitors (Patent Documents 1, 2, 3 and 4). Several of these have already been used practically as diabetes therapeutics. On the other hand, there are known DPP-4 inhibitors derived from natural products, such as a gelatin-derived peptide (Patent Document 5), a milk casein-derived peptide (Patent Document 6), a hydrolyzable tannin (Patent Document 7), and extracts of paprika and other plants (Patent Document 8). In addition, a product obtained by hydrolyzing a protein using a known method has also been reported to be able to be used for the prevention and/or treatment of symptoms mediated by DPP-4 (Patent Document 9).

Patent Document 1: JP 2005-5003211 T
Patent Document 2: JP 2004-535455 T
Patent Document 3: JP 2004-536115 T
Patent Document 4: JP 2000-327689 A
Patent Document 5: WO 2008/066070
Patent Document 6: JP 2007-39424 A
Patent Document 7: JP 2008-280291 A
Patent Document 8: JP 2007-277163 A
Patent Document 9: JP 2008-500304 T
Non-Patent Document 1: Journal of Pharmacological Sciences, 125, 379-384 (2005)
Non-Patent Document 2: Expert Opin. Investig Drugs, 1091-1102 (2004)

SUMMARY OF THE INVENTION

The present invention aims to provide a DPP-4 inhibitor that is produced using a natural product that has been eaten, as a raw material and that is suitable for oral applications not only in terms of DPP-4 inhibitory activity but also from the viewpoints of flavor and absorbability, and a composition (such as a food or beverage, functional food, pharmaceutical, enteral nutrient or animal feed) for the prevention and/or amelioration of diabetes which contains the DPP-4 inhibitor.

As a result of conducting extensive studies to solve the above-mentioned problems, the inventors of the present invention have found that a product obtained by breaking a peptide bond of a protein present in a specific type of bean through hydrolysis with a microorganism or a proteolytic enzyme derived from the microorganism has a DPP-4 inhibitory effect, and that the product is superior in terms of flavor as well, thereby leading to completion of the present invention.

Namely, the present invention relates to a DPP-4 inhibitor, obtained by treating an azuki bean or a kidney bean with a microorganism or a proteolytic enzyme produced by the microorganism. The microorganism is preferably one or more types selected from the group consisting of koji molds, lactic acid bacteria, and natto bacteria, and the proteolytic enzyme is preferably one or more enzymes derived from one or more types of microorganisms selected from the group consisting of koji molds, lactic acid bacteria, and natto bacteria. In addition, the present invention also relates to a DPP-4 inhibitor, obtained by treating a soybean with a koji mold or a proteolytic enzyme derived from the koji mold.

Moreover, the present invention also relates to a method of producing a DPP-4 inhibitor, which comprises treating an azuki bean or a kidney bean with a microorganism or a proteolytic enzyme produced by the microorganism.

According to the present invention, a DPP-4 inhibitor having superior DPP-4 inhibitory activity, and a food or beverage, functional food, pharmaceutical, animal feed or the like containing the DPP-4 inhibitor as an active ingredient, are provided by treating a specific type of bean that has been eaten, with a microorganism that has also been commonly used in food or an enzyme derived, from the microorganism. The DPP-4 inhibitor of the present invention is not only superior in terms of safety in consideration of the above, but is also suitable for oral ingestion in particular from the viewpoints of flavor and absorbability. The DPP-4 inhibitor of the present invention is useful as an active ingredient of a composition for the prevention and/or amelioration of diabetes.

BEST MODE FOR CARRYING OUT THE INVENTION

The following provides a detailed explanation of the present invention.

The DPP-4 inhibitor of the present invention is obtained by treating an azuki bean or a kidney bean with a microorganism or a proteolytic enzyme produced by the microorganism. In other words, the present invention is also directed to a method of producing a DPP-4 inhibitor, which comprises treating an azuki bean or a kidney bean with a microorganism or a proteolytic enzyme produced by the microorganism. In the present invention, a product that has been fragmented (reduced in molecular weight) by hydrolysis of a peptide bond of a protein in the above bean is thought to be involved as the active ingredient of the DPP-4 inhibitor. Thus, a DPP-4 inhibitor containing as an active ingredient a protein hydrolysate derived from an azuki bean or a kidney bean is also included in the scope of the present invention.

In the present invention, although there are no particular limitations on the microorganism used to treat an azuki bean or a kidney bean, a microorganism that produces a proteolytic enzyme is preferred, and from the viewpoint of safety, a microorganism used in food production is preferred. Specific examples of such microorganisms include koji molds, lactic acid bacteria, and natto bacteria. Among these, koji molds are particularly preferred.

Also in the present invention, although there are no particular limitations on the proteolytic enzyme used to treat an azuki bean or a kidney bean, provided it is a microorganism-derived proteolytic enzyme capable of hydrolyzing a peptide bond, a proteolytic enzyme derived from a koji mold, a lactic acid bacterium, or a natto bacterium is preferred, and a proteolytic enzyme derived from a koji mold is more preferred.

Moreover, a product obtained by treating a soybean with a koji mold or a proteolytic enzyme derived from the koji mold can also be used as the DPP-4 inhibitor in the present invention.

There are no particular limitations on the koji mold used in the present invention or the koji mold from which an enzyme used in the present invention is derived, provided it is related to the production of food in Japan or overseas and is safe. Examples thereof include, for example, ones used in the production of soy sauce, miso (fermented soybean paste), or alcohol. Specific examples of such koji molds include molds of the genus *Aspergillus* such as *Aspergillus oryzae, Aspergillus sojae, Aspergillus kawachii, Aspergillus oryzae, Aspergillus sojae, Aspergillus kawachii, Aspergillus awamori, Aspergillus tamari* and *Aspergillus glaucus*, as well as red koji molds. In particular, koji molds used to produce soy sauce are preferably used because of their high protease activity, *Aspergillus oryzae* and *Aspergillus sojae* are more preferably used, and *Aspergillus oryzae* is particularly preferably used. In addition, so-called "koji (rice malt)" or "koji starter," in which a koji mold as mentioned above is grown on a bean, rice, wheat, barley, bran, or the like, may also be used.

There are no particular limitations on the lactic acid bacterium used in the present invention or the lactic acid bacterium from which an enzyme used in the present invention is derived, provided it is a bacterium that produces lactic acid by metabolism. Specific examples thereof include bacteria of the genera *Lactobacillus, Bifidobacterium, Enterococcus, Lactococcus, Pediococcus* and *Leuconostoc*.

In addition, examples of the natto bacterium used in the present invention or the natto bacterium from which an enzyme used in the present invention is derived, include *Bacillus subtilis* var. *natto*.

Typical examples of proteolytic enzymes include peptidases capable of hydrolyzing a peptide bond of a peptide and proteases capable of hydrolyzing a peptide bond of a protein. The proteolytic enzyme used in the present invention may be a single peptidase purified or a single protease purified, or may be a composition containing two or more members selected from the group consisting of peptidases, proteases and the like. In addition, the proteolytic enzyme may also be a composition that contains another enzyme to an extent that does not impair the activity of the peptidase or protease. A commercially available product as described later can be used for the proteolytic enzyme used, or a treated cell product or a partially purified enzyme which is obtained by disrupting or partially purifying a microorganism that produces a proteolytic enzyme may also be used. Moreover, a treated cell product of a recombinant microorganism that produces a proteolytic enzyme or an enzyme derived from the recombinant microorganism may also be used. Production of the recombinant microorganism can be carried out by using an ordinary genetic engineering technique.

It is preferable to degrade a protein into peptides with lower molecular weights in order for the protein to be easily absorbed in the gastrointestinal tract by degradation. From this viewpoint, the proteolytic enzyme used in the present invention preferably includes a peptidase.

In addition, it is generally known that the vicinities of a proline residue in a protein are less likely to undergo the action of a protease or peptidase. X-prolyl dipeptidyl aminopeptidase is an enzyme that specifically releases X-proline dipeptides (where X represents an arbitrary amino acid residue) from the amino terminal, and a proteolytic enzyme having this enzyme activity is thought to more easily reduce the molecular weight of a protein. From this viewpoint, the microorganism or the proteolytic enzyme used in the present invention more preferably has X-prolyl dipeptidyl aminopeptidase activity. It is noted that *Aspergillus oryzae* has been reported to produce X-prolyl dipeptidyl aminopeptidase (H. Tachi, Phytochemistry, 31(11), 3707-3709 (1992)).

In the case of using a commercially available proteolytic enzyme in the present invention, although there are no particular limitations on the type of commercially available proteolytic enzyme, those which are commercially available as food additives can be suitably used. Examples thereof include Umamizyme G, Protease A "Amano" G, Protease A "Amano" SD, Protease M "Amano" G, and Protease M "Amano" SD (all of which are manufactured by Amano Enzyme Inc.), Sumizyme LP, Sumizyme FP, and Sumizyme LPL (all of which are manufactured by Shin Nihon Chemical Co., Ltd.), Pantidase NP-2 (manufactured by Yakult Pharmaceutical Industry Co., Ltd.) and Orientase ONS (manufactured by HBI Enzyme Inc.). Furthermore, such a proteolytic enzyme can be used in the present invention even if its form has been altered. The proteolytic enzyme may be in the form of granules, powder or liquid. The proteolytic enzyme can be used in the present invention provided it is able to hydrolyze a protein.

Among the above-mentioned proteolytic enzymes, Umamizyme G is more suitably used because of its strong X-prolyl dipeptidyl aminopeptidase activity.

With respect to the azuki bean, soybean or kidney bean which may be used as a raw material for the DPP-4 inhibitor of the present invention, the azuki bean refers to *Vigna angularis*, the soybean refers to *Glycine max*, and the kidney bean refers to *Phaseolus vulgaris*, and examples of the kidney bean include cultivars such as tora beans, otebo beans, uzura beans (pinto beans) and ofuku beans. Also with respect to the soybean, since there is a lack of adequate data pertaining to safety and allergenicity when proteins of genetically modified soybeans (GMO soybeans) are hydrolyzed by microorganisms or proteases derived from the microorganisms, a non-genetically modified (non-GMO) soybean is preferably used. In addition, non-GMO soybeans can be more suitably used than GMO soybeans from the viewpoints of DPP-4 inhibitory activity and flavor.

The above-mentioned beans usable in the present invention may be used as is for the raw material, or alternatively compositions produced by using beans as raw materials, such as natto (fermented soybeans), soy sauce, soy milk, bean jam and other similar products, and foods consisting of residues that remain following the production of other foods from beans, such as okara (soybean curd residue) and defatted soybeans, may be used as raw materials.

Although the above-mentioned beans can be used as is as raw materials for producing the DPP-4 inhibitor of the present invention, they may also undergo pretreatment such as drying, crushing, grinding, heating, pressurizing, defatting, acid treatment, alkali treatment, pressing or extraction. In addition, two or more types of these pretreatments may be carried out in combination. Moreover, the above-mentioned bean materials can be used as raw materials for producing the DPP-4 inhibitor of the present invention after separating protein or a fraction containing a large amount of protein therefrom.

In the present invention, there are no particular limitations on the method used to treat the above-mentioned bean with a microorganism. For example, a method may be employed in which a bean material is pretreated in the manner described above as necessary, a microorganism is allowed to grow on the surface of the bean material, and water is added to the grown microorganism for further reaction, whereby a peptide bond of a protein present in the bean is broken by hydrolysis. Moreover, other examples thereof include a method in which a microorganism is grown in a bean material or treated bean material suspended and/or dissolved in a liquid such as water, and a method in which a microorganism is grown in a liquid processed bean product.

In addition, there are no particular limitations on the method used to treat the bean with a proteolytic enzyme in the present invention. For example, a method may be employed in which a bean material is pretreated in the manner described above as necessary, and a proteolytic enzyme is sprinkled on the surface of the bean material, or the proteolytic enzyme is allowed to act on the bean material or treated bean material suspended and/or dissolved in a liquid such as water, whereby a peptide bond of a protein present in the bean is broken by hydrolysis, as well as a method in which a proteolytic enzyme is added to a liquid processed bean product.

In the present invention, although the product treated with a microorganism or a proteolytic enzyme obtained according to the method described above can be used as is as a DPP-4 inhibitor, it may also be subjected to deodorization, decolorization or the like within a range that does not cause a loss of DPP-4 inhibitory activity. In addition, fractionation using a method such as extraction, precipitation, filtration, ultrafiltration or column chromatography, or a combination thereof, may be carried out in order to concentrate the component having DPP-4 inhibitory activity.

The DPP-4 activity can be measured by, for example, adding glycyl-L-proline 4-methylcoumaryl-7-amide as substrate to human DPP-4 enzyme and incubating the mixture, followed by assaying the amount of 7-amino-4-methylcoumarin formed using a spectrofluorimeter. In the present invention, a comparison is made in the assay between the DPP-4 activities in the case in which a specimen to be evaluated for DPP-4 inhibitory activity is present (sample) and the case in which it is not present (vehicle control), and a sample that significantly lowers DPP-4 activity with respect to the DPP-4 activity of the vehicle control is evaluated as "having DPP-4 inhibitory activity." The DPP-4 activity of a sample for the DPP-4 inhibitor of the present invention based on a value of 100% for the DPP-4 activity of a vehicle control is preferably 70% or less, more preferably 60% or less and particularly preferably 50% or less.

In addition, in a preferred aspect, the DPP-4 inhibitor of the present invention may also have α-glucosidase inhibitory activity in addition to DPP-4 inhibitory activity. This α-glucosidase activity can be measured by, for example, adding sucrose as substrate to yeast-derived α-glucosidase and incubating the mixture, followed by assaying the amount of glucose formed with a commercially available glucose assay kit. In the present invention, a comparison is made in the assay between the α-glucosidase activities in the case in which a specimen to be evaluated for α-glucosidase inhibitory activity is present (sample) and the case in which it is not present (vehicle control), and a sample that significantly lowers α-glucosidase activity with respect to the α-glucosidase activity of the vehicle control is evaluated as "having α-glucosidase inhibitory activity." The DPP-4 inhibitor of the present invention preferably also has α-glucosidase inhibitory activity such that the α-glucosidase activity of a sample based on a value of 100% for the α-glucosidase activity of a vehicle control is 90% or less and more preferably 80% or less.

In general, production processes used to obtain peptides by hydrolyzing a protein are known to be susceptible to the generation of a bitter taste or unpleasant odor. However, the DPP-4 inhibitor of the present invention, which is obtained by treating an azuki bean or a kidney bean with a microorganism or a proteolytic enzyme produced by the microorganism, and the DPP-4 inhibitor of the present invention, which is obtained by treating a soybean with a koji mold or a proteolytic enzyme derived from the koji mold, have a less bitter taste or less unpleasant odor, and in the case of using a koji mold or a proteolytic enzyme derived from the koji mold in particular, a DPP-4 inhibitor can be produced that has a superior flavor. Thus, the DPP-4 inhibitor of the present invention can be particularly favorably used for a composition for oral ingestion for which having a superior flavor is preferred. The composition for oral ingestion herein refers to a composition orally ingested by humans, livestock, pets or the like, and specific examples thereof include foods and beverages, pharmaceuticals, animal feeds and the like.

The DPP-4 inhibitor of the present invention may be used as a composition for oral ingestion as described above, or may be used as a composition that is administered directly into the gastrointestinal tract and absorbed therefrom in the manner of an enteral nutrient. In addition, although it may be used as is as a food or beverage, pharmaceutical, animal feed or the like, it may also be used in the form of a composition containing it in applications such as foods and beverages, pharmaceuticals and animal feeds. In the case of using the DPP-4 inhibitor of the present invention in applications described above, there are no particular limitations on the form thereof, and for example, it may be used as a food or beverage in the form of a general food or a supplement such as a functional food (e.g. food with health claims (food for specified health uses, food with nutrient function claims), health food, nutritional supplement, sports supplement). Alternatively, it may be used as a pharmaceutical in the form of a prescription pharmaceutical, an easily acquired drug or quasi drug such as an OTC drug, or a cosmetic or the like.

In the case of ingesting the DPP-4 inhibitor of the present invention as a general food or functional food, it may be ingested directly or may be ingested in the form of a composition in which it is mixed with a known additive (e.g. carrier, adjuvant) by molding into an easily taken form such as a capsule, tablet or granule. In addition, it may also be used after adding and combining with any vitamin such as vitamin A, C, D or E for the purpose of nutritional enrichment. Moreover, it may also be compounded with another functional food or the like. Although there are no particular limitations on other functional foods compounded therewith, examples include known functional foods having metabolic regulatory effects such as blood sugar lowering effect, lipid lowering effect or anti-obesity effect, blood pressure lowering effect, osteoporosis preventive and/or ameliorative effect, or the like.

Moreover, the DPP-4 inhibitor of the present invention may be used in general foods by mixing with food or beverage materials, examples of which include confections such as chewing gum, chocolate, candy, jelly, cookies or crackers; frozen confections such as ice cream or ice candy; beverages such as tea, soft drinks, nutritional drinks or beauty drinks; noodles such as udon noodles, Chinese noodles, spaghetti or instant noodles; fish jelly products such as kamaboko (boiled fish paste), chikuwa (tube-shaped fish cakes) or hanpen (ground fish cakes); condiments such as salad dressing, mayonnaise or sauce; and oils and fats such as margarine, butter or salad oil; as well as bread, ham, soup, pre-cooked foods and frozen foods.

In the case of using the DPP-4 inhibitor of the present invention as a pharmaceutical, there are no particular limitations on the form thereof, and examples include capsules, tablets, granules, injections, suppositories and patches. When formulating a preparation, other pharmaceutically acceptable preparation materials can be appropriately added, examples of which include excipients, disintegrating agents, lubricants, binders, antioxidants, colorants, dispersing agents, absorption promoters, dissolution promoters and stabilizers.

Moreover, in the case of using the DPP-4 inhibitor of the present invention as a pharmaceutical, it may be compounded with another pharmaceutical such as an anti-diabetic drug, anti-obesity drug or anti-osteoporosis drug. There are no particular limitations on anti-diabetic drugs or anti-obesity drugs as other pharmaceuticals, and examples thereof include sulfonylurea drugs, biguanide drugs, α-glucosidase inhibitors, insulin preparations, insulin secretion promoters, insulin sensitizers, PPAR agonists (such as PPARα agonists, PPARγ agonists or PPARα+γ agonists), β3 adrenergic receptor agonists, aldose reductase inhibitors, DPP-4 inhibitors, AMP kinase activators, 11 beta-hydroxysteroid dehydrogenase type 1 (11 beta-HSD-1) inhibitors, lipase inhibitors and appetite suppressants. Examples of anti-osteoporosis drugs include activated vitamin D3 preparations, estrogen preparations, selective estrogen receptor modulators, bisphosphonate preparations, vitamin K2 preparations and calcium preparations.

α-glucosidase is an enzyme that degrades disaccharides such as maltose or sucrose into monosaccharides in the intestine. Since inhibiting α-glucosidase makes it possible to inhibit absorption of polysaccharides and disaccharides and thereby significantly inhibit postprandial hyperglycemia, it is known to be effective in preventing or ameliorating diabetes. However, as is clear from their mechanism of action, α-glucosidase inhibitors are not recognized to demonstrate effects against increases in blood sugar levels attributable to glucose intake. In addition, α-glucosidase inhibitors also have limitations on the manner in which they are taken, such as being unable to demonstrate their effects unless ingested immediately before eating. The DPP-4 inhibitor of the present invention not only has an effect against increases in blood sugar levels attributable to glucose intake, but also offers the considerable advantage of not being subjected to limitations on the timing for administration. Moreover, the DPP-4 inhibitor of the present invention can be expected to demonstrate a more potent blood sugar lowering effect since it more preferably has both DPP-4 inhibitory activity and α-glucosidase inhibitory activity as previously described.

On the basis of the above, a composition containing the DPP-4 inhibitor of the present invention can be used as a composition for the prevention and/or amelioration of diabetes. In addition, the DPP-4 inhibitor of the present invention can also be used as a blood sugar elevation inhibitor, hypoglycemic agent, insulin secretion promoter, active GLP-1 content-increasing agent, glucagon secretion inhibitor, pancreatic 0 cell regeneration promoter and/or agent promoting sugar uptake by muscle.

Further, the present invention is also directed to a method for the prevention and/or amelioration of diabetes, which comprises administrating to a subject the above-mentioned DPP-4 inhibitor. In addition, the present invention is also directed to a method for inhibiting an increase in blood sugar level, which comprises administration of the above-mentioned DPP-4 inhibitor to a subject. The scope of the prevention of diabetes includes reducing the risk of onset of diabetes. In addition, although preferred examples of the subject in the above cases include diabetes patients and persons at risk for diabetes (persons having blood sugar levels at the high end of the normal range and persons having been indicated as being at high risk for diabetes on the basis of genetic factors or lifestyle), the subject may also be a healthy individual.

EXAMPLES

The following provides a more detailed explanation of the present invention by way of examples, but the present invention is not limited to the examples.

(Measurement of DPP-4 Inhibitory Activity)

In the present invention, the DPP-4 inhibitory activity was evaluated by measuring the DPP-4 activity using a commercially available assay kit (DPP-4 Drug Discovery Kit, Biomol) in accordance with the instructions provided with the kit and then comparing measured values. The following provides a brief description of the measurement method.

Amounts of 50 μL (for blank), 35 μL (for control), and 25 μL (for sample), of buffer (50 mM Tris, pH 7.5) were placed in the respective wells of a white 96-well half area plate provided with the kit. Next, after adding 10 μL of a sample to the sample wells, 15 μL of an enzyme solution (human DPP-4 enzyme) was added to the control wells and the sample wells followed by mixing well with a plate mixer. Next, 50 µL of glycyl-L-proline 4-methylcoumaryl-7-amide serving as a DPP-4 substrate was added to all of the wells (total liquid volume in each well: 100 µL) followed by allowing the enzyme reaction to proceed by incubating at 37° C. The incubation was carried out in a temperature-controllable fluorescence intensity measuring device (Powerscan HT, Dainippon Pharmaceutical Co., Ltd.), and measurements were carried out immediately after the start of incubation and 12 minutes later at an excitation wavelength of 380 nm and a measuring wavelength of 460 nm to measure the amount of 7-amino-4-methylcoumarin formed as a result of the enzyme reaction.

Here, the DPP-4 activity of a sample was calculated in the manner indicated below based on a value of 100% for the value of DPP-4 activity of the control.

$$DPP\text{-}4\ \text{activity}(\%)=\{(A-B)/(C-D)\}\times 100$$

In the equation, A represents a fluorescence intensity of the sample well at 12 minutes after the start of incubation, B represents a fluorescence intensity of the sample well immediately after the start of incubation, C represents a fluorescence intensity of the control well at 12 minutes after the start of incubation, and D represents a fluorescence intensity of the control well immediately after the start of incubation. This equation shows that a lower value for DPP-4 activity indicates more potent inhibitory activity.

EXAMPLE 1

Preparation of Koji Mold-Treated Beans

After steaming 1 kg each of commercially available soybean, azuki bean, otebo bean, ofuku bean, murasakihana bean (scarlet runner bean) and winged bean, coarsely crushing and adjusting to a moisture content of about 50% by adding the respective roasted and crushed product as necessary, each bean was placed in a container equipped with a filter that allows sterile air to pass through, followed by autoclaving at high pressure for 30 minutes at 121° C. Next, 3 g of a wheatbran koji obtained using a koji mold (Aspergillus oryzae KBN616, Bio'c Co., Ltd.) was inoculated onto the sterilized raw material in a clean bench for preventing contamination by microorganisms other than the koji mold, followed by fermenting with only the koji mold for 48 hours at 31° C. while supplying sterile air to the container.

Subsequently, 75 g of each of the fermentation products obtained in the clean bench was transferred to a sterile glass container followed by the addition of 150 mL of sterile distilled water, sealing with a silicon rubber stopper, and treating for 3 days at 30° C. under conditions in which microorganisms other than the koji mold were not present and without adding salt to obtain a koji mold-treated liquid.

Subsequently, after heating the koji mold-treated liquids for 30 minutes at 90° C., the liquids were filtered to obtain clear liquids. These liquids were then fractionated by centrifuging for 100 minutes at 14000 G using a centrifugal ultrafiltration device with a molecular weight cutoff of 3000 (MICROCON® YM-3 Filter Unit, MILLIPORE™ Corp.), and the resulting filtrates were freeze-dried to obtain koji mold-treated beans. Each of the resulting koji mold-treated beans was dissolved in water to a concentration of 10 mg/mL to give a sample (concentration on measurement of DPP-4 activity: 1 mg/mL), and the DPP-4 inhibitory activity of each sample was then evaluated according to the method previously described. The results are shown in Table 1.

TABLE 1

|  | DPP-4 Activity (%) |
| --- | --- |
| Koji mold-treated soybean 1 mg/mL | 59.0 |
| Koji mold-treated azuki bean 1 mg/mL | 38.8 |
| Koji mold-treated otebo bean 1 mg/mL | 62.2 |
| Koji mold-treated ofuku bean 1 mg/mL | 56.5 |
| Koji mold-treated murasakihana bean 1 mg/mL | 70.3 |
| Koji mold-treated winged bean 1 mg/mL | 75.9 |

This shows that the koji mold-treated products of the soybean, azuki bean, and some kidney beans (otebo bean and ofuku bean) had DPP-4 inhibitory activity, and their inhibitory activities were higher than those of the koji mold-treated products of other beans (murasakihana bean and winged bean) used for the purpose of comparison.

EXAMPLE 2

Preparation of Proteolytic Enzyme-Treated Beans

After crushing 3 g each of commercially available azuki bean, tora bean and otebo bean with a mill, the beans were autoclaved for 15 minutes at 121° C. After placing each autoclaved bean in a container, 30 mL of water and 3 mL of a separately prepared proteolytic enzyme solution (UMAMIZYMEN® G Enzyme, Amano Enzyme Inc., 1% w/v aqueous solution) were added. After incubating for 24 hours at 45° C., the reaction mixture was centrifuged for 30 minutes at 1800 G to remove any residue that had not degraded. After recovering the supernatant and heating for 60 minutes at 99° C., the mixture was again centrifuged for 30 minutes at 1800 G followed by recovery of the supernatant. Filtrates obtained by fractionating the recovered supernatants by centrifuging for 60 minutes at 1800 G using a centrifugal ultrafiltration device with a molecular weight cutoff of 10000 (AMICON® ULTRA-15 Filtration Device, MILLIPORE™ Corp.) were then freeze-dried to obtain proteolytic enzyme-treated beans. Each of the enzyme-treated beans was then dissolved in water to a concentration of 10 mg/mL or 30 mg/mL to give a sample (concentration on measurement of DPP-4 activity: 1 mg/mL and 3 mg/mL), and the DPP-4 inhibitory activity of each sample was then evaluated according to the method previously described. The results are shown in Table 2.

TABLE 2

|  | DPP-4 Activity (%) |
| --- | --- |
| Enzyme-treated azuki bean 3 mg/mL | 16.1 |
| Enzyme-treated azuki bean 1 mg/mL | 48.9 |
| Enzyme-treated tora bean 3 mg/mL | 30.0 |
| Enzyme-treated tora bean 1 mg/mL | 66.9 |
| Enzyme-treated otebo bean 3 mg/mL | 32.1 |
| Enzyme-treated otebo bean 1 mg/mL | 70.1 |

This shows that the proteolytic enzyme-treated products of the azuki bean, tora bean, and otebo bean all had DPP-4 inhibitory activity.

EXAMPLE 3

Preparation of Proteolytic Enzyme-Treated Beans (Preparation of Samples Undergoing Changes Over Time)

After crushing 3 g each of commercially available azuki bean, tora bean and otebo bean with a mill, the beans were autoclaved for 15 minutes at 121° C. After placing each autoclaved bean in a container, 30 mL of water and 3 mL of a separately prepared proteolytic enzyme solution (UMAMIZYME® G Enzyme, Amano Enzyme Inc., 1% w/v aqueous solution) were added. Incubation of the mixture was then started at 45° C. After sampling 1 mL aliquots of the reaction mixture before the start of incubation and 24 hours after the start of incubation, each sample was, then heated for 60 minutes at 99° C., and then centrifuged for 10 minutes at 14000 G followed by recovery of the supernatant. The supernatants were then fractionated by centrifuging for 100 minutes at 14000 G using a centrifugal ultrafiltration device with a molecular weight cutoff of 3000 (MICROCON® YM-3 Filter Unit, MILLIPORE™ Corp.) to obtain filtrates. The filtrates were then directly evaluated for DPP-4 inhibitory activity according to the method previously described and compared between the inhibitory activities before and after the enzyme treatment. The results are shown in Table 3.

TABLE 3

|  | DPP-4 Activity (%) |
|---|---|
| Before enzyme treatment of azuki bean | 107.1 |
| After 24 hours of enzyme treatment of azuki bean | 60.7 |
| Before enzyme treatment of tora bean | 110.0 |
| After 24 hours of enzyme treatment of tora bean | 64.6 |
| Before enzyme treatment of otebo bean | 108.3 |
| After 24 hours of enzyme treatment of otebo bean | 73.1 |

None of the azuki bean, tora bean and otebo bean were observed to have DPP-4 inhibitory activity before the enzyme treatment, while DPP-4 inhibitory activity was observed after 24 hours of enzyme treatment. That is, it was clearly shown that DPP-4 inhibitory activity was not observed in water extracts of the azuki bean and kidney beans, but rather only appeared as a result of treating each of the azuki bean and kidney beans with the enzyme.

EXAMPLE 4

Animal Evaluation Study

The enzyme-treated azuki bean, tora bean and otebo bean prepared in Example 2 and an enzyme-treated defatted soybean prepared using the same method as Example 2 were evaluated for their actual blood sugar lowering effects in the body by using an oral glucose tolerance test. C57BL/6J SPF male mice (Clea Japan, Inc.) were used at age 10 weeks for the study animals. Twenty mice were divided into four groups of 5 mice each. In a single experiment, evaluation was carried out on four groups consisting of a control group (administered distilled water), a positive control group (administered sitagliptin) and two sample groups. Two experiments were carried out and a total of four samples were evaluated.

Blood samples were collected from the caudal veins of the mice that had been fasting since the previous evening, and blood sugar levels were measured using a simple blood glucose measuring device (GLUTEST ACE®, Sanwa Kagaku Kenkyusho Co., Ltd.) to determine pretest values (0 minutes). 100 mg tablets of sitagliptin (MERCK) were ground with a mortar and suspended in water to a concentration of 0.1 mg/mL as sitagliptin for use as a positive control. Each of the enzyme-treated beans prepared in Example 2 (or in accordance with the method thereof) was dissolved with distilled water to a concentration of 400 mg/mL for use as an administration sample. Distilled water (control group), the sitagliptin suspension (positive control group) or the enzyme-treated bean aqueous solution (sample group) was administered orally at 10 mL/kg of body weight. A 40% aqueous glucose solution was administered orally at 5 mL/kg of body weight 30 minutes after administering the distilled water, sitagliptin suspension, or sample. Blood samples were collected from the caudal veins of the mice at, 30, 60 and 120 minutes after the oral administration of glucose, followed by measurement of these blood sugar levels in the same manner as that used for measurement of pretest values. The results of measuring blood sugar levels are shown in Table 4.

TABLE 4

| Time elapsed after glucose administration | 0 minutes (pretest value) | 30 minutes | 60 minutes | 120 minutes |
|---|---|---|---|---|
| Experiment 1 | | | | |
| Control | 80.4 ± 6.2 | 390.6 ± 13.7 | 293.8 ± 32.7 | 136.4 ± 8.1 |
| Sitagliptin | 82.4 ± 7.0 | 270.6 ± 24.2*** | 185.4 ± 16.2* | 110.2 ± 12.3 |
| Enzyme-treated defatted soybean | 71.8 ± 5.0 | 297.0 ± 16.1** | 234.6 ± 28.1 | 130.6 ± 5.6 |
| Enzyme-treated azuki bean | 69.0 ± 4.1 | 286.4 ± 16.3** | 192.6 ± 7.9* | 105.4 ± 5.8* |
| Experiment 2 | | | | |
| Control | 79.8 ± 7.4 | 386.8 ± 46.7 | 316.2 ± 35.1 | 127.2 ± 3.8 |
| Sitagliptin | 72.0 ± 4.7 | 215.4 ± 8.5*** | 145.0 ± 8.9* | 93.6 ± 8.7** |
| Enzyme-treated tora bean | 81.6 ± 1.3 | 289.8 ± 11.8* | 231.8 ± 26.0 | 114.4 ± 6.6 |
| Enzyme-treated otebo bean | 79.0 ± 6.0 | 255.0 ± 6.7** | 191.4 ± 12.0** | 107 ± 7.0 |

Values represented as mean ± standard error
Statistically significant difference (vs. control) *P < 0.05, P < 0.01, *P < 0.001

The proteolytic enzyme-treated products of the defatted soybean, azuki bean, tora bean and otebo bean all significantly inhibited increases in blood sugar levels following glucose loading. In particular, the effect of inhibiting increases in blood sugar levels was found to be superior for the proteolytic enzyme-treated azuki bean.

EXAMPLE 5

Measurement of α-Glucosidase Inhibition

Each of the proteolytic enzyme-treated azuki bean prepared in Example 2 and an enzyme-treated defatted soybean prepared using the same method as Example 2 was dissolved in 0.25 M phosphate buffer (pH 6.8) used as assay buffer to a concentration of 16.7 mg/mL to give a sample. Measurement of α-glucosidase activity was carried out in the manner described below. Specifically, 60 μL of the sample was added to wells of a 96-well plate while 60 μL of assay buffer was added to wells for control. Subsequently, 20 μL of yeast-derived α-glucosidase (Oriental Yeast Co., Ltd.) adjusted to a concentration of 1.25 U/mL (10 μg protein/mL) was added followed by incubating for 10 minutes at 37° C. Next, 20 μL of a 250 mM solution of sucrose in assay buffer was added followed by incubating for 20 minutes at 37° C. (the concentration of each enzyme-treated product during the reaction was 10 mg/mL). Following completion of incubation, 100 μL of 2 M Tris-HCl buffer (pH 7.0) was added to stop the reaction. After stopping the reaction, 50 μL of the reaction liquid in each well was transferred to a separate 96-well plate followed by the addition of 200 μL of a Glucose CII Test Wako reagent (Wako Pure Chemical Industries, Ltd.) and incubating for 5 minutes at 37° C. Following completion of incubation, the absorbance at 505 nm was measured, and the amount of glucose formed was determined from a calibration curve prepared using glucose standards. Furthermore, the α-glucosidase activity was calculated as indicated below based on a value of 100% for the value of α-glucosidase activity of the control.

$$\alpha\text{-Glucosidase activity}(\%) = (A/B) \times 100$$

In the above equation, A represents the amount of glucose of a sample, and B represents the amount of glucose of the control. This equation shows that a lower value for α-glucosidase activity (%) indicates more potent inhibitory activity. The results are shown

TABLE 5

| | alpha-Glucosidase activity (%) |
|---|---|
| Enzyme-treated defatted soybean (10 mg/mL) | 10.0 |
| Enzyme-treated azuki bean (10 mg/mL) | 6.5 |

This shows that both the enzyme-treated defatted soybean and the enzyme-treated azuki bean demonstrated α-glucosidase inhibitory activity.

EXAMPLE 6

Flavor Comparison of Proteolytic Enzyme-Treated Azuki Bean and Soybean

An amount of 6 g of a commercially available azuki bean was crushed with a mill and then autoclaved for 15 minutes at 121° C. The sterilized material was divided into two portions, and after placing each portion in a separate container, 30 mL of water and 3 mL of a separately prepared proteolytic enzyme solution (a 1% w/v aqueous solution of UMAMIZYME® G Enzyme (Amano Enzyme Inc., koji mold-derived protease) or a 1% w/v aqueous solution of Bromelain F (Amano Enzyme Inc., pineapple-derived protease)) were added to each container. After incubating for 24 hours at 45° C., the reaction mixture was centrifuged for 30 minutes at 1800 G to remove any residue that had not degraded. After recovering the supernatant and heating for 60 minutes at 99° C., the mixture was again centrifuged for 30 minutes at 1800 G followed by recovery of the supernatant. Filtrates obtained by fractionating the recovered supernatants by centrifuging for 60 minutes at 1800 G using a centrifugal ultrafiltration device with a molecular weight cutoff of 10000 (AMICON® ULTRA-15 Filtration Device, MILLIPORE™ Corp.) were freeze-dried to obtain enzyme-treated azuki beans. Two types of enzyme-treated soybeans were also prepared in the same manner.

A test to assess bitter taste was carried out in the form of a sensory evaluation of the resulting enzyme-treated products by five panelists. Evaluations were carried out by scoring according to the criteria indicated below and calculating the average score of the five panelists.
5: No bitter taste perceived
4: Hardly any bitter taste perceived
3: Unable to determine presence of bitter taste
2: Somewhat bitter taste perceived
1: Bitter taste perceived
The results are shown in Table 6.

TABLE 6

| | Proteolytic enzyme used | |
|---|---|---|
| Enzyme-treated azuki beans | Umamizyme G | Bromelain F |
| Panelist 1 | 5 | 3 |
| Panelist 2 | 4 | 2 |
| Panelist 3 | 5 | 2 |
| Panelist 4 | 4 | 1 |
| Panelist 5 | 5 | 2 |
| Average | 4.6 | 2.0 |

| | Proteolytic enzyme used | |
|---|---|---|
| Enzyme-treated soybeans | Umamizyme G | Bromelain F |
| Panelist 1 | 4 | 2 |
| Panelist 2 | 3 | 1 |
| Panelist 3 | 4 | 2 |
| Panelist 4 | 4 | 2 |
| Panelist 5 | 4 | 2 |
| Average | 3.8 | 1.8 |

This shows that in the case of both the enzyme-treated azuki beans and the enzyme-treated soybeans, the enzyme-treated product obtained using a koji mold-derived enzyme (Umamizyme) was superior in terms of having a less bitter taste in comparison with the enzyme-treated product obtained using a plant-derived enzyme (Bromelain). In addition, the enzyme-treated azuki bean was superior to the enzyme-treated soybean with respect to having a less bitter taste.

What is claimed is:

1. A method for the amelioration of diabetes and/or inhibiting blood glucose elevation, comprising administrating to a subject a protein hydrolysate derived from an azuki bean or a kidney bean, which is a dipeptidyl peptidase-4 (DPP-4) inhibitor and which is obtained by the method comprising treating an azuki bean, a kidney bean or a treated bean thereof, suspended or dissolved in water, with a proteolytic enzyme produced by a koji mold, wherein the proteolytic enzyme has X-prolyl dipeptidyl aminopeptidase activity.

2. The method for the amelioration of diabetes and/or inhibiting blood glucose elevation according to claim 1, wherein the koji mold is *Aspergillus oryzae* or *Aspergillus sojae*.

* * * * *